US011850307B2

(12) United States Patent
Helsper et al.

(10) Patent No.: US 11,850,307 B2
(45) Date of Patent: Dec. 26, 2023

(54) MULTI-DOSAGE TABLET ARRAY

(71) Applicant: ALFASAN NEDERLAND B.V., Utrecht (NL)

(72) Inventors: Freek Helsper, Utrecht (NL); Anthonie Sebastiaan Tesink, Utrecht (NL)

(73) Assignee: ALFASAN NEDERLAND B.V., Woerden (NL)

( * ) Notice: Subject to any disclaimer, the term of this patent is extended or adjusted under 35 U.S.C. 154(b) by 0 days.

(21) Appl. No.: 17/905,904

(22) PCT Filed: Mar. 9, 2021

(86) PCT No.: PCT/EP2021/055944
§ 371 (c)(1),
(2) Date: Sep. 8, 2022

(87) PCT Pub. No.: WO2021/180736
PCT Pub. Date: Sep. 16, 2021

(65) Prior Publication Data
US 2023/0123598 A1  Apr. 20, 2023

(30) Foreign Application Priority Data

Mar. 10, 2020 (EP) .................................. 20162131

(51) Int. Cl.
*A61K 9/20* (2006.01)
(52) U.S. Cl.
CPC .............. *A61K 9/20* (2013.01); *A61J 2205/20* (2013.01)
(58) Field of Classification Search
CPC ......... A61K 9/20; A61J 7/0076; A61J 7/0084; A61J 7/0069; A61J 2200/74; A61J 2205/20
See application file for complete search history.

(56) References Cited

U.S. PATENT DOCUMENTS

| | | | |
|---|---|---|---|
| 2003/0175326 A1* | 9/2003 | Thombre | A23K 50/40 424/442 |
| 2007/0221722 A1 | 9/2007 | Rodney et al. | |
| 2019/0183735 A1 | 6/2019 | Mogilefsky et al. | |

OTHER PUBLICATIONS

Hazewinkel et al., Reduced Dosage of Ketoprofen for the Short-Term and Long-Term Treatment of Joint Pain in Dogs, Jan. 4, 2003, The Veterinary Record, pp. 11-14 (Year: 2003).*

(Continued)

*Primary Examiner* — Toan M Le
(74) *Attorney, Agent, or Firm* — BROWDY AND NEIMARK, PLLC

(57) ABSTRACT

Described is a multi-dosage array of tablets comprising one or more active substances, the tablets being coated and void of tablet portioning means so as to avoid contact of the tablet constituents upon handling by a user for the provision of a plurality of different dosages of the one or more active substances to a plurality of patients of different weight who are in need of the said one or more active substances, the dosage being dependent on the weight of the respective patient, the array of tablets comprising three or more tablet groups, each tablet group consisting of identical tablets having unique identification means and a unique dosage of the one or more active substances, the said tablets differing from tablets of another group of the array in at least the dosage of the said two or more active substances and in the identification means. Further described are a multi-dosage tablet array system, a medicament dosage comprising a plurality of the tablets of the multi-dosage array of tablets, a dosage comprising a plurality of the tablets of the multi-dosage tablet array, a method of providing a dosage of one or more active substances tailored to the body weight of a patient and a method of providing a tailored dosage of one or more active substances to the body weight of a patient.

14 Claims, 2 Drawing Sheets

(56) References Cited

OTHER PUBLICATIONS

Simpson et al., Effects of Reconcile (Fluoxetine) Chewable Tablets Plus Behavior Management for Canine Separation Anxiety, Spring 2007, Veterinary Therapeutics, vol. 8, No. 1, pp. 18-31 (Year: 2007).*

Zoetis Inc.: "Clavamox (amoxicillin and clavulanate potassium tablets)" Sep. 2017 (Sep. 2017), XP055803031, Retrieved from the Internet: <URL:https://www.zoetisus.com/products/dogs/clavamox/resources/clavamox-combined-mark>.

* cited by examiner

|  | Tab A | Tab B | Tab C | Tab D |
|---|---|---|---|---|
| < 2 kg | ○ | | | |
| 3-4 kg | ○ ○ | | | |
| 5 kg | | ● | | |
| 6-7 kg | ○ | ● | | |
| 8-10 kg | | | ◉ | |
| 11-12 kg | ○ | | ◉ | |
| 13-15 kg | | ● | ◉ | |
| 16-17 kg | ○ | ● | ◉ | |
| 18-20 kg | | | | ⊖ |
| 21-22 kg | ○ | | | ⊖ |
| 23-24 kg | ○ ○ | | | ⊖ |
| 25 kg | | ● | | ⊖ |
| 26-27 kg | ○ | ● | | ⊖ |
| 28-30 kg | | | ◉ | ⊖ |
| 31-35 kg | | ● | ◉ | ⊖ |
| 36-40 kg | | | | ⊖ ⊖ |
| 41-45 kg | | ● | | ⊖ ⊖ |
| 46-50 kg | | | ◉ | ⊖ ⊖ |
| 51-60 kg | | | | ⊖ ⊖ ⊖ |
| 61-70 kg | | | ◉ | ⊖ ⊖ ⊖ |
| 71-80 kg | | | | ⊖ ⊖ ⊖ ⊖ |

Figure 1

| 2A | Prednisolone 1 mg/kg ||||
|---|---|---|---|---|
| | 2 mg | 5 mg | 10 mg | 20 mg |
| | Tab 1 | Tab 2 | Tab 3 | Tab 4 |
| 2 kg | ○ | | | |
| 4 kg | ○○ | | | |
| 5 kg | | ● | | |
| 7 kg | ○ | ● | | |
| 10 kg | | | ◍ | |
| 12 kg | ○ | | ◍ | |
| 15 kg | | ● | ◍ | |
| 20 kg | | | | ◉ |
| 30 kg | | | ◍ | ◉ |
| 40 kg | | | | ◉◉ |

| 2B | Amoxillin 10 mg/kg ||||
|---|---|---|---|---|
| | 10 mg | 50 mg | 100 mg | 200 mg |
| | Tab 1 | Tab 2 | Tab 3 | Tab 4 |
| 2 kg | ○ | | | |
| 4 kg | ○○ | | | |
| 5 kg | | ● | | |
| 7 kg | ○ | ● | | |
| 10 kg | | | ◍ | |
| 12 kg | ○ | | ◍ | |
| 15 kg | | ● | ◍ | |
| 20 kg | | | | ◉ |
| 30 kg | | | ◍ | ◉ |
| 40 kg | | | | ◉◉ |

| 2C | Benazepril 0.25/kg ||||
|---|---|---|---|---|
| | 0.5 mg | 1.25 mg | 2.5 mg | 5.0 mg |
| | Tab 1 | Tab 3 | Tab 3 | Tab 4 |
| 2 kg | ○ | | | |
| 4 kg | ○○ | | | |
| 5 kg | | ● | | |
| 7 kg | ○ | ● | | |
| 10 kg | | | ◍ | |
| 12 kg | ○ | | ◍ | |
| 15 kg | | ● | ◍ | |
| 20 kg | | | | ◉ |
| 30 kg | | | ◍ | ◉ |
| 40 kg | | | | ◉◉ |

Figure 2

MULTI-DOSAGE TABLET ARRAY

The invention relates to a multi-dosage array of tablets, to a multi-dosage tablet array system comprising a plurality of multi-dosage arrays of tablets, a dosage of one or more active substances comprising a plurality of tablets of the multi-dosage tablet array, to a method of providing a dosage of one or more active substances for a patient and a method of providing a dosage of one or more active substances tailored to the body weight of a patient.

In medicine, in particular in the veterinary world, there is increasing attention to the user safety of medicine products. In many cases, skin contact with the medicament is to be avoided, and the user is often advised to wear gloves. This is in particular the case for (veterinary) hospital personnel that handle medicaments for a plurality of patients.

In particular in veterinary medicine, where the weight of the patients differ significantly, medicaments are provided as tablets that are intended to be broken in predetermined portions by the presence of portioning means, such as one or more break lines. When breaking such a tablet, it is inevitable that the user comes in contact with the constituents of the tablet, which is undesired.

Especially in the case of high-active substances such as hormones, in particular corticosteroids, antibacterial agents, antihypertensive agents, non-steroidal anti-inflammatory drugs, antifungal agents, anti-epileptics, analgesics and thyroid drugs there is a significant risk for health implications to the user. For this reason, the use of tablets as described above is discouraged.

Providing a proper dosage of one or more active substances, dependent on the weight of the patients that each differ in weight is therefore cumbersome. This is particularly true when the patients significantly vary in weight, and many different dosages have to be available.

The above problem is solved by the provision of a multi-dosage array of tablets comprising one or more active substances, the tablets being coated and void of tablet portioning means so as to avoid contact of the tablet constituents upon handling by a user for the provision of a plurality of different dosages of the one or more active substances to a plurality of patients of different weight who are in need of the said one or more active substances, the dosage being dependent on the weight of the respective patient, the array of tablets comprising three or more tablet groups, each tablet group consisting of identical tablets having unique identification means and a unique dosage of the one or more active substances, the said tablets differing from tablets of another group of the array in at least the dosage of the said two or more active substances and in the identification means, wherein the dosage of the one or more active substances in the tablets of the second group is 2.5 times the dosage of the said one or more active substances in the tablets of the first group, and the dosage of the one or more active substances in the tablets of the third group is twice the dosage of the said one or more active substances in the tablets of the second group.

The invention provides one or more active substances in tablet form in a series of dosages, where the tablets prohibit contact of the skin of the user with the ingredients of the tables by the presence of a coating and are not intended be broken manually because of the absence of portioning means. The absence of such means discourages the user to try to break the tablets. In addition, breaking is not necessary as the multi-dosage tablet array of the invention provides for tablets of a different dosage, as the array comprises multiple tablet groups wherein the tablets, each of a unique dosage. This way, tablets of different tablet groups of the multi-dosage tablet array, i.e. tablets comprising a different dosage of the same medicament are provided, so that any envisaged dosage can be obtained by the combination of multiple tablets from the array.

Herein, the user can be the patient himself, in particular if the patient is human. However, for veterinary purposes, the user is usually the veterinarian or the owner or caretaker of the animal. The tablet comprises one or more active substances, herein also referred to as medicaments.

The tablets of the array are coated so as to avoid contact of the tablet constituents, including ingredients that should not be in contact with the skin, in particular the active ingredient. As such, tablet coating is generally known. However, coatings are mainly used to mask taste or colour change of tablets. It is however not known to apply a coating with the aim to avoid contact of the tablet constituents with the user. These measures are intended to avoid direct contact of a user with the active substance of the tablet. It is commonly known that an envisaged dosage of the active substance depends on the body weight of the patient. In particular in veterinary medicine, the weight range of animals of the same species can vary extremely, in particular for e.g. dogs. In the art, the medicaments (i.e. for dogs) usually comprise proportioning means such as breaking lines in order to provide a dose for the smaller patients. Breaking of tablets results in undesired contact of the user with the active substance.

The present invention provides an array of tablets, the array comprising tablet groups and in each tablet group, the tablets have a dose for an envisaged body weight of the patient, and the dosage differs per tablet group such, that there is a first tablet group for an envisaged body weight, a second tablet group comprising a dosage 2.5 times that of the first group, and a third group comprising a dosage having a double dosage as compared to the second group, and the tablets of each group can be discriminated from one another by identification means that are unique for each tablet group.

E.g. the first group may comprise a dosage of an active substance for an envisaged body weight of 2 kg, the second group will have a dosage for an envisaged body weight of 5 kg and the third group for an envisaged body weight of 10 kg. Such an array enables the user to combine tablets from said different groups to arrive at a dosage for a patient of a particular body weight. A patient having a body weight of 4 kg will need 2 tablets from the first group, a patient having a body weight of 7 kg will need a tablet from the first group and one from the second group, a patient having a body weight of 12 kg need a tablet from both the first and the third group etc. As the tablets of the different groups have identification means that discriminate the tablets from different groups, the combination of different tablets is very convenient.

As such, arrays of medicaments are known in the art. US2019/0183735 describes a dosage management system intended for a single human user, wherein tablets of different dosages can be present that differ from one another e.g. in size, shape or colour. However, such system provides for higher dosages if the user/patient occasionally needs a higher dose than usual, and it can be seen whether a particular tablet has been taken or not. However, the problem of providing a plurality of different dosages for a plurality of different patients that differ significantly in weight is not provided. Only tablets with double the dosage are present in this known system. The provision of tablets that only double the dosage does not provide a versatile array of tablets that can de used to combine to a dosage, tailored to virtually any envisaged body weight of patients. In contrast, the tablets of this known system are intended for a single patient, i.e. having a constant weight.

In order to avoid undesired mixing and confusion between the tablets of different groups, the tablets of the different groups can be discriminated and be identified from one another, in particular by visual means. To this end, the tablets of each of the groups have unique identification means, such as colour, shape, weight, form or a combination thereof. The unique visual identification means preferably comprise the tablet colour. As the tablets comprise a coating, the coating of the tablets of different groups can be different in colour. Such colour discrimination facilitates the proper choice and combination of the tablets without the risk of mixing up tablets of different groups. The use of visually discriminative tablets reduces the chance of dosing errors.

Any medicament that is to be administered in tablet form is suitable for the tablets of the multiple-dosage tablet array of the invention. In particular, corticosteroids, such as prednisone, prednisolone, dexamethasone; antibacterial agents, such as metronidazole, amoxicillin, doxycycline; antihypertensive agents, such as benazepril, amlodipine, telmisartan; non-steroidal anti-inflammatory drugs (NSAIDs), such as meloxicam, carprofen, firocoxib; antifungal agents, such as miconazole, terbinafine, ketoconazole; anti-epileptics, such as fenobarbital; analgesics, such as tramadol, methadone; and thyroid drugs, such as thiamazole, (L)-thyroxine.

As each of the tablet group has tablets of a unique dosage that differs from tablets from another group of the tablet array, a combination of tablets, in particular from different groups provide the envisaged dosage of the medicaments or combination of two or more medicaments without the need to break the tablets or to come into contact with the tablet constituents in another way.

The tablet array comprises at least 3 tablet groups wherein the dosage of the one or more active substances in the tablets of the second group is 2.5 times the dosage of the said one or more active substances in the tablets of the first group, and the dosage of the one or more active substances in the tablets of the third group is twice the dosage of the said one or more active substances in the tablets of the second group. By such a combination of tablet groups, almost any desired dosage of a medicament or combination of two or more medicaments can be combined with a relatively low number of tablets, which is advantageous for patient compliance and ease of use.

Advantageously, the tablet array comprises at least 4 tablet groups, wherein the dosage of the one or more active substances in the tablets of the fourth group is twice the dosage of the said one or more active substances in the tablets of the first group. By such dosages in the tablet groups, dosages varying with a factor 1-100 can advantageously be prepared without the need for braking the tablets, while still providing tailored dosages for a vast range of body weights of the patients.

In an attractive embodiment, the tablet array comprises an additional tablet group wherein the dosage of the one or more active ingredients in the tablets of the said additional group is half the dosage of the said one or more active substances in the tablets of the first group. By the provision of such an additional group, it becomes also possible to provide tailored dosages for very light patients without the need of breaking tablets.

By the provision of such different tablet groups, virtually any envisaged dosage tailored for any patient of whatever body weight can be provided, where the dosage is in conformity with the body weight.

In a very attractive embodiment, the invention provides a multi-dosage tablet array system that comprises a plurality of multi-dosage arrays of tablets as described above, wherein the tablets of each array differ in one or more active substances or in ratio between the said two or more active substances as compared to tablets belonging to another array, each array comprising tablet groups having a dosage of the respective one or more active substances, tailored for a predetermined body weight of a patient, wherein tablets of groups of the different arrays, the dosage of the one or more active substances of said tablets being tailored for the same predetermined body weight comprise the same identification means. Such array systems allow a very convenient methodology for dosing multiple active substances or medicaments or combinations of two or more medicaments in different tablets, and to provide for a single dosing system based on the unique identification means for different medicaments or combinations of two or more medicaments based on the patient's body weight. According to this embodiment, the tablets belonging to different arrays, i.e. comprising different medicaments or combinations of two or more medicaments, will have the same identification means when the tablets are intended for the same body weight of the patient. This means that a very convenient system is provided for combination of tablets to arrive at an envisaged dosage, based on the body weight, which system is applicable for a plurality of different medicaments. In particular, such a system enables the provision of a plurality of different medicaments that all share the same identification means for a dosage intended for a specific weight of the target patient.

The array system of the invention comprises multiple tablet arrays, wherein each array comprises tablets with a unique active substance or combination of two or more active substances, wherein the each of the tablet groups of each array comprise a dose of the respective active substance of that array for the same envisaged body weight of the patient. So the first tablet groups of the array of an array system will all comprise a dosage of the respective active substance for the same envisaged body weight of the patient, and these will have the same identification means. Such an array system highly facilitates the provision of the proper amount of tablets that comprise different active substances, as for each tablet array, the combination of different tablets to arrive at the dosage of a patient of a particular body weight is the same for each tablet array.

The term 'predetermined body weight' here also encompasses a portion of the total body weight of a patient. Accordingly, a tablet of the one group of an array (i.e. with a blue colour as identification means) can have a dosage for a predetermined body weight of 5 kg, and a tablet of another group of the same array (with another identification means, such as another colour, such as yellow) can have a dosage of the same active substance for a predetermined body weight for the said species of e.g. 10 kg. Another array of the same system will comprise another active substance (or combination) and will comprise blue tablets comprising a dose tailored for an envisaged body weight of 5 kg, and yellow tablets comprising a dose for a predetermined body weight of 10 kg. The envisaged patient, such a dog, having a total body weight of 15 kg in need of the medicament of the one group will receive a yellow tablet for 10 kg (predetermined weight) and a blue one for 5 kg predetermined weight. If the dog needs also the medicament of the other array, again a red and a blue tablet of the said array will be given. The combination of predetermined weights add up to the total weight of the envisaged patient. In another example, in this system, tablets having an active ingredient against a particular disease in dogs, which are dosed for a dog of 2 kg, can have the identification of the colour red. So any tablet in this system, dosed for a dog of 2 kg will have the same identification, here the red colour. The tablets having a dose of a medicament for a dog of 5 kg will have another identification means, such as a blue colour. So tablets having different active ingredients and intended to be used for different diseases for the same target patient species such as a dog comprising a dose for the same body weight, e.g. 2 kg, will be red, and those for a dog of 5 kg will be blue. So irrespective the contents of the tablet, the dosing will be universal. For a dog of 9 kg, one blue and two red tablets are to be given. If the said dog of 9 kg needs different tablets, i.e. for treatment of two different diseases, the dog will receive tablets from two different arrays, i.e. a blue tablet and two red tablets of each of the arrays. By this, dosing becomes universal.

The multiple dosage tablet array is very suitable for any patient species, as individual patients differ in weight and may need a different dosages for a particular medicament. The multi-dose tablet array or array system as described above is particularly suitable when the patients belong to the same genus, in particular the same species, as the body weight-based dosage of the active substances is usually constant among species. The array is suitable for human application, but in particular for animals, where the body weight may vary more, more in particular for animal species wherein the body weight varies significantly within the species. The multi-dose tablet array is therefore particularly suitable for veterinary purposes, as in veterinary medicine, animals of a broad range of different weight are to be treated with the same active medicaments in tablet form. As indicated above, this is usually achieved by breaking the tablets.

Suitable animals are e.g. farm animals, such as cattle, horse, sheep, pigs, goats etc. and companion animals, such as dogs, cats, rabbits, etc. The average weight of a dog is 20 kg, but there is a wide variation between breeds. The average weight of a cat is 5 kg, and here again there is variation in weight. Because of the vast variety in body weight, the multi-dose tablet array is particularly suitable for feline or canine patients, in particular canine.

In particular for veterinary medicine, e.g. for administration to dogs and cats, a preferred embodiment provides a multi-dose tablet array wherein the tablets of the first group have a dosage of the one or more active substances tailored for a patient having a body weight of about 2 kg. This means that a single tablet has such a dosage that a single tablet is intended for administration to a patient having a body weight of 2 kg. Accordingly, the dosage of the one or more active substances in the tablets of the second group equals the dosage for 5 kg body weight of the target patient, i.e. meaning that a single tablet is envisaged to arrive at the envisaged dosage for a patient having a body weight of 5 kg. The dosage of the medicament or combination of two or more medicaments in the tablets of the third group would then equal the dosage for 10 kg body weight of the target patient, the dosage of the medicament or combination of two or more medicaments in the tablets of the fourth group, if present, equals the dosage for 20 kg body weight of the target patient, and if present, the dosage of the medicament or combination of two or more medicaments in the tablets of the additional group equals the dosage for 1 kg body weight of the target patient. By these tablet groups, a suitable dose for virtually any patient of any body weight can be provided.

The invention also relates to a dosage of one or more active substances comprising a plurality of the tablets of the multi-dosage array of the array system as described above.

In another embodiment, a method of providing a dosage of one or more active substances for a patient, the dosage being tailored to the body weight of the patient, comprising a plurality of tablets from the multi-dosage array of tablets or from the array system as described above is provided, wherein the dosage is tailored to the body weight of the patient and comprises a plurality of tablets from the multi-dosage tablet array or array system. Such a tailored dosage is obtained by the proper combination of tablets from different tablet groups, or by multiple tablets from a single group, or a combination thereof.

The invention also relates to a method of providing a dosage of one or more active substances tailored to the body weight of a patient, comprising the steps a) determining the weight of the patient and b) combining a plurality of tablets from one or more multi-dosage tablet arrays such that the dosage of the said plurality of tablets from each array corresponds with the patient weight determined in step a). As indicated above, tablets of different groups are preferably combined to arrive at the envisaged dosage; thereto, step b) preferably comprises combining tablets from different tablet groups from the one or more multi-dosage tablet arrays.

FIG. 1 shows a dosing scheme of a multi-dosage tablet array as described above, comprising four tablet groups (A-D), each indicated by unique visual identification means, allowing the tablets from the different groups to be discriminated from one another. Tablets of group A (open circles) have a medicament dosage that is tailored for (i.e. corresponds with) a body weight of up to 2 kg for an envisaged patient, e.g. 8 mg. Tablets of group B (circles with dots) have a dosage that is tailored for a body weight of 5 kg for the same envisaged patient, in this example 20 mg. Tablets of group C (hatched circles) have a dosage that is tailored for a body weight of 10 kg for the same envisaged patient, in this example 40 mg, and tablets of group D (circle with horizontal lines) have a dosage that is tailored for a body weight of 20 kg for the same envisaged patient, in this example 80 mg. By combination of tablets from one or more groups, almost any body weight-dependent dosage can be obtained. By providing another multi-dosage tablet array, comprising tablets having another medicament or medicament combination, the very same dosing scheme can be applied. Of course, the dosage of the medicaments can vary per array, as for the one medicament 8 mg is suitable for 2 kg body weight, whereas for another medicament only 2 mg may be suitable for that body weight of 2 kg. The arrays and system that comprises different arrays highly facilitate the proper dosing of tableted medicaments for patients, without being in contact with any critical compounds of the tablet constituents and without the need of further manipulation of the tablets.

FIG. 2 shows a multi-dosage array system for three different medicaments, each array comprising four tablet groups, the tablets of the first group (Tab 1) being red (open circles), of the second group (Tab 2) being blue (dotted circles), of the third group (Tab 3) being yellow (hatched circles) and of the fourth group (Tab 4) being green (lined circles). The first array, shown in FIG. 2A, comprises tablets comprising the active substance prednisolone for dogs, wherein the dose corresponds with 1 mg/kg. The first (red) tablet group has a prednisolone dosage of 2 mg, i.e. tailored for a predetermined body weight of 2 kg of the dog. The second (blue) tablet group has a dosage of 5 mg, i.e. tailored for a predetermined body weight of 5 kg of the dog. The third (yellow) tablet group has a dosage of 10 mg, i.e. tailored for a predetermined body weight of 10 kg of the dog. The fourth (green) tablet group has a dosage of 20 mg, i.e.

tailored for a predetermined body weight of 20 kg of the dog. As can be seen in FIG. 2A, a dog of 4 kg total body weight will receive two prednisolone tablets of the first tablet group, each tablet being dosed for a predetermined body weight of 2 kg. A dog of 7 kg will receive a single tablet from group 1 and a single tablet from group 2. Accordingly, a dog of 15 kg will receive a single tablet from group 2 and a single tablet from group 5. Accordingly, a dog having a body weight of 17 kg will receive an additional tablet from the first tablet group. A large dog of 40 kg will receive 2 green tablets.

In FIG. 2B, a second array of the system is shown wherein the tablets comprise the active substance amoxicillin for dogs and cats, wherein the dose corresponds with 10 mg/kg. The first (red) tablet group has an amoxicillin dosage of 20 mg, i.e. tailored for a predetermined body weight of 2 kg of the dog or cat. The second (blue) tablet group has a dosage of 50 mg, i.e. tailored for a predetermined body weight of 5 kg of the dog/cat. The third (yellow) tablet group has a dosage of 100 mg, i.e. tailored for a predetermined body weight of 10 kg of the dog/cat. The fourth (green) tablet group has a dosage of 200 mg, i.e. tailored for a predetermined body weight of 20 kg of the dog/cat. As can be seen in FIG. 2B, a dog or cat of 4 kg total body weight will receive two amoxicillin tablets of the first tablet group, each tablet being dosed for a predetermined body weight of 2 kg. A dog or cat of 7 kg will receive a single tablet from group 1 and a single tablet from group 2. Accordingly, a dog or cat of 15 kg will receive a single tablet from group 2 and a single tablet from group 5, and a dog or cat having a body weight of 17 kg will receive an additional tablet from the first tablet group.

In FIG. 2C, a third array of the system is shown wherein the tablets comprise the active substance benazepril for dogs and cats, wherein the dose corresponds with 0.25 mg/kg. The first (red) tablet group has an amoxicillin dosage of 0.5 mg, i.e. tailored for a predetermined body weight of 2 kg of the dog or cat. The second (blue) tablet group has a dosage of 1.25 mg, i.e. tailored for a predetermined body weight of 5 kg of the dog/cat. The third (yellow) tablet group has a dosage of 2.5 mg, i.e. tailored for a predetermined body weight of 10 kg of the dog/cat. The fourth (green) tablet group has a dosage of 5 mg, i.e. tailored for a predetermined body weight of 20 kg of the dog/cat. As can be seen in FIG. 2B, a dog or cat of 4 kg total body weight will receive two benazepril tablets of the first tablet group, each tablet being dosed for a predetermined body weight of 2 kg. A dog or cat of 7 kg will receive a single tablet from group 1 and a single tablet from group 2. Accordingly, a dog or cat of 15 kg will receive a single tablet from group 2 and a single tablet from group 5, and a dog or cat having a body weight of 17 kg will receive an additional tablet from the first tablet group.

The invention claimed is:

1. A multi-dosage tablet array system, comprising:
a plurality of multi-dosage arrays of tablets, each said tablet being coated and void of tablet portioning means, and each having one or more veterinary active substances for a treatment of an intended animal patient, all of the tablets in a single multi-dosage array having the same active substances, and all of the tablets in each different multi-dosage array having differing active substances,
wherein each said multi-dosage array of tablets comprises three or more tablet groups, each said tablet group consisting of a plurality of identical tablets, each having a dosage of the one or more active substances tailored for a predetermined body weight of the intended animal patient, and an identifier that identifies the corresponding dosage, whereby tablets in the same tablet group having the same dosage also have the same identifier,
wherein each of the tablets of each tablet group differ from each of the tablets of another tablet group within each said multi-dosage array in the dosage of the said one or more active substances and in the identifier, the dosage in the tablets of each tablet group being tailored to a different predetermined body weight of the intended animal patient and having a different identifier, and
wherein the three or more tablet groups within each said multi-dosage array include tablet groups with dosages of the one or more active substances characteristic of that array, tailored to the same predetermined body weights of the intended animal patient, and the tablets of each tablet group of each said multi-dosage array that have a dosage tailored to the same predetermined body weight, having the same identifier.

2. The multi-dosage tablet array system of claim 1, wherein in each said multi-dosage array, the dosage of the one or more active substances in the tablets of the second tablet group is 2.5 times the dosage of the said one or more active substances in the tablets of the first tablet group, and the dosage of the one or more active substances in the tablets of the third tablet group is twice the dosage of the said one or more active substances in the tablets of the second tablet group.

3. The multi-dosage tablet array system of claim 1, wherein the identifier comprises a visual identifier.

4. The multi-dosage tablet array system of claim 3, wherein the visual identifier is the tablet color.

5. The multi-dosage tablet array system of claim 1, wherein each said multi-dosage tablet array comprises at least 4 tablet groups, wherein the dosage of the one or more active substances in the tablets of the fourth tablet group is twice the dosage of the said one or more active substances in the tablets of the third tablet group.

6. The multi-dosage tablet array system of claim 1, wherein each said multi-dosage tablet array comprises an additional tablet group wherein the dosage of the one or more active ingredients in the tablets of the said additional tablet group is half the dosage of the said one or more active substances in the tablets of the first tablet group.

7. The multi-dosage tablet array system of claim 1, wherein the animal patients of different weight belong to the same species.

8. The multi-dosage tablet array system of claim 1, wherein the animal patients of different weight are companion animals.

9. The multi-dosage tablet array system of claim 8, wherein the animal patients of different weight are canine.

10. The multi-dosage tablet array system of claim 1, wherein the tablets of the first tablet group of each of said multi-dosage arrays have a dosage of the one or more active substances tailored for an animal patient having a body weight of about 2 kg.

11. A dosage of a plurality of active substances comprising a plurality of the tablets of one or more arrays of the array system of claim 1.

12. A method of providing a dosage of a plurality of active substances for an animal patient, comprising providing a plurality of tablets from one or more of the multi-dosage tablet array system of claim 1.

13. A method of providing a dosage of a plurality of active substances tailored to the body weight of an animal patient according to claim 12, comprising the steps of:
   determining the weight of the animal patient, and
   combining a plurality of tablets from one or more of said multi-dosage arrays of tablets, such that the dosage of the one or more active substances of the said plurality of tablets from each array corresponds with the animal patient weight determined in said determining step.

14. The method of claim 13, wherein said combining step comprises combining tablets from different tablet groups from the one or more multi-dosage arrays of tablets.

* * * * *